(12) United States Patent
Mark et al.

(10) Patent No.: US 10,835,634 B2
(45) Date of Patent: Nov. 17, 2020

(54) METHOD FOR THE AGGLOMERATION OF SUPERABSORBER PARTICLES

(71) Applicant: BASF SE, Ludwigshafen (DE)

(72) Inventors: Tina Mark, Hassloch (DE); Thomas Daniel, Waldsee (DE); Erich Lutz, Altrip (DE); Stefan Molter, Maxdorf (DE)

(73) Assignee: BASF SE, Ludwigshafen (DE)

( * ) Notice: Subject to any disclaimer, the term of this patent is extended or adjusted under 35 U.S.C. 154(b) by 446 days.

(21) Appl. No.: 15/564,212

(22) PCT Filed: Mar. 24, 2016

(86) PCT No.: PCT/EP2016/056509
§ 371 (c)(1),
(2) Date: Oct. 4, 2017

(87) PCT Pub. No.: WO2016/162218
PCT Pub. Date: Oct. 13, 2016

(65) Prior Publication Data
US 2018/0126032 A1    May 10, 2018

(30) Foreign Application Priority Data
Apr. 7, 2015  (EP) .................................. 15162595

(51) Int. Cl.
| | |
|---|---|
| *A61L 15/60* | (2006.01) |
| *C08F 265/06* | (2006.01) |
| *C08F 6/18* | (2006.01) |
| *C08L 51/00* | (2006.01) |
| *C08L 101/14* | (2006.01) |
| *C08F 265/04* | (2006.01) |
| *A61L 15/22* | (2006.01) |

(52) U.S. Cl.
CPC .............. *A61L 15/60* (2013.01); *A61L 15/22* (2013.01); *C08F 6/18* (2013.01); *C08F 265/04* (2013.01); *C08F 265/06* (2013.01); *C08L 51/003* (2013.01); *C08L 101/14* (2013.01)

(58) Field of Classification Search
CPC ........ C08J 3/12; C08J 2300/14; C08F 265/02; C08F 265/04; C08F 265/06; C08F 220/06; C08F 222/385; C08F 6/18; C08L 51/003; C08L 101/14; A61L 15/22; A61L 15/60
See application file for complete search history.

(56) References Cited

U.S. PATENT DOCUMENTS

| 5,455,284 | A | 10/1995 | Dahmen et al. | |
|---|---|---|---|---|
| 2008/0188586 | A1* | 8/2008 | Bruhns | ................... A61L 15/60 522/153 |
| 2009/0105389 | A1* | 4/2009 | Walden | ................. C08L 101/14 524/437 |
| 2010/0234531 | A1* | 9/2010 | Frank | ....................... B01J 20/26 525/192 |
| 2012/0118832 | A1* | 5/2012 | Yontz | .................. B01J 20/2803 210/728 |

FOREIGN PATENT DOCUMENTS

| EP | 0 807 646 | A1 | 11/1997 |
|---|---|---|---|
| EP | 1 878 761 | A1 | 1/2008 |
| WO | WO-92/01008 | A1 | 1/1992 |
| WO | WO-2005/092955 | A1 | 10/2005 |
| WO | WO-2006/014031 | A1 | 2/2006 |

OTHER PUBLICATIONS

Buchholz, Fredric L., et al. *Modern Superabsorbent Polymer Technology*, "Commercial Processes for the Manufacture of Superabsorbent Polymers." New York: John Wiley & Sons, Inc., 1998, pp. 69-117.
International Search Report for Patent Application No. PCT/EP2016/056509, dated Jun. 16, 2016.

* cited by examiner

*Primary Examiner* — Anthony J Zimmer
*Assistant Examiner* — Syed T Iqbal
(74) *Attorney, Agent, or Firm* — Marshall, Gerstein & Borun LLP

(57) ABSTRACT

A process for agglomerating superabsorbent particles, wherein polymer particles having a particle size of 250 μm or less are dispersed in a hydrophobic organic solvent, the dispersed polymer particles are mixed with an aqueous monomer solution, the total amount of water applied to the dispersed polymer particles being at least 100% by weight, based on the dispersed polymer particles, and the monomer solution is polymerized.

20 Claims, No Drawings

METHOD FOR THE AGGLOMERATION OF SUPERABSORBER PARTICLES

CROSS-REFERENCE TO RELATED APPLICATIONS

This application is the U.S. National Phase of PCT/EP2016/056509, filed Mar. 24, 2016, which claims the benefit of European Patent Application No. 15162595.1, filed Apr. 7, 2015.

The present invention relates to a process for agglomerating superabsorbent particles, wherein polymer particles having a particle size of 250 μm or less are dispersed in a hydrophobic organic solvent, the dispersed polymer particles are mixed with an aqueous monomer solution, the total amount of water applied to the dispersed polymer particles being at least 100% by weight, based on the dispersed polymer particles, and the monomer solution is polymerized.

The production of superabsorbent particles is described in the monograph "Modern Superabsorbent Polymer Technology", F. L. Buchholz and A. T. Graham, Wiley-VCH, 1998, pages 69 to 117. The superabsorbent particles are typically produced by solution polymerization or suspension polymerization.

Being products which absorb aqueous solutions, superabsorbents are used to produce diapers, tampons, sanitary napkins and other hygiene articles, but also as water-retaining agents in market gardening.

The properties of the water-absorbing polymers may be altered via the level of crosslinking. As the level of crosslinking increases, gel strength increases and absorption capacity decreases.

To improve the use properties, for example permeability in the swollen gel bed in the diaper and absorption under pressure, superabsorbent particles are generally surface postcrosslinked. This increases only the level of crosslinking of the particle surface, and in this way it is possible to at least partly decouple absorption under pressure and centrifuge retention capacity.

EP 0 807 646 A1 describes a process for suspension polymerization in the presence of polymer particles.

WO 2005/092955 A1 describes a process for producing superabsorbent particles by solution polymerization. The superabsorbent particles can be agglomerated by addition of an aqueous solution before or after surface postcrosslinking, the water content of the superabsorbent particles being kept within the range from 1% to 10% by weight.

WO 2006/014031 A1 describes a process for producing superabsorbent particles by suspension polymerization. The superabsorbent particles can be agglomerated by addition of an aqueous solution before or after surface postcrosslinking, the water content of the superabsorbent particles being kept within the range from 1% to 10% by weight.

It was an object of the present invention to provide an improved process for agglomerating superabsorbent particles, wherein the superabsorbent particles are especially to have a high absorption capacity.

It was a further object of the present invention to provide an improved process for agglomerating superabsorbent particles, wherein especially excessively small polymer particles ("fines") removed from other processes are utilized.

The object was achieved by a process for agglomerating superabsorbent particles by polymerizing an aqueous monomer solution 1 comprising a) at least one ethylenically unsaturated monomer which bears acid groups and may have been at least partly neutralized, b) optionally one or more crosslinkers, c) at least one initiator, d) optionally one or more ethylenically unsaturated monomers copolymerizable with the monomers mentioned under a) and e) optionally one or more water-soluble polymers, and optionally drying and/or comminuting the resulting polymer particles, which comprises removing polymer particles having a particle size of 250 μm or less, dispersing the polymer particles removed in a hydrophobic organic solvent, mixing the dispersed polymer particles with an aqueous monomer solution 2 comprising a) at least one ethylenically unsaturated monomer which bears acid groups and may have been at least partly neutralized, b) optionally one or more crosslinkers, c) at least one initiator, d) optionally one or more ethylenically unsaturated monomers copolymerizable with the monomers mentioned under a) and e) optionally one or more water-soluble polymers, where monomer solution 1 and monomer solution 2 may be the same or different, the total amount of water applied to the dispersed polymer particles being at least 100% by weight, based on the dispersed polymer particles, and polymerizing monomer solution 2.

Polymer particles having a particle size of preferably 200 μm or less, more preferably 150 μm or less and most preferably 120 μm or less are removed. The particle size can be removed by means of a sieve having the corresponding mesh size. Polymer particles which pass through a sieve having a mesh size of x μm accordingly have a particle size of x μm or less.

The polymer particles can be removed by means of a sieve having a mesh size of 250 μm or less, preferably 200 μm or less, more preferably 150 μm or less and most preferably 120 μm or less.

The total amount of water applied to the dispersed polymer particles is preferably at least 150% by weight, more preferably at least 175% by weight, very preferably at least 200% by weight, based in each case on the dispersed polymer particles.

The water may be added exclusively with monomer solution 2. Besides monomer solution 2, however, it is also possible to use a further aqueous solution or water. The solutions can be metered simultaneously or in succession. For example, the dispersed polymer particles can be pre-swollen with addition of water and then mixed with monomer solution 2.

The amount of monomer a) applied with monomer solution 2 ought not to substantially exceed the amount of dispersed polymer particles. Otherwise there is a risk that no agglomerates will form. The amount of monomer a) applied with monomer solution 2 is preferably from 1% to 150% by weight, more preferably from 2% to 100% by weight and most preferably from 5% to 80% by weight, based in each case on the amount of dispersed polymer particles.

The present invention is based on the finding that the amount of water applied with monomer solution 2 has a considerable influence on the centrifuge retention capacity (CRC) of the agglomerates.

The production of the superabsorbent particles is elucidated hereinafter:

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The acid groups of the monomers a) may have been partly neutralized. The neutralization is conducted at the monomer stage. This is typically accomplished by mixing in the neutralizing agent as an aqueous solution or else preferably as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomers a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, methylenebisacrylamide, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are methylenebisacrylamide and the polyethoxylated and/or -propoxylated glycerols which have been esterified with acrylic acid or methacrylic acid to give di- or triacrylates, as described, for example, in WO 2003/104301 A1. Methylenebisacrylamide and di- and/or triacrylates of 3- to 10-tuply ethoxylated glycerol are particularly advantageous. Very particular preference is given to methylenebisacrylamide, di- or triacrylates of 1- to 5-tuply ethoxylated and/or propoxylated glycerol. Most preferred are methylenebisacrylamide and the triacrylates of 3- to 5-tuply ethoxylated and/or propoxylated glycerol, especially methylenebisacrylamide and the triacrylate of 3-tuply ethoxylated glycerol.

The amount of crosslinker b) in monomer solution 1 is preferably 0.0001% to 0.5% by weight, more preferably 0.001% to 0.2% by weight and most preferably 0.01% to 0.05% by weight, based in each case on unneutralized monomer a). With rising crosslinker content, the centrifuge retention capacity (CRC) falls and the absorption under a pressure of 21.0 g/cm$^2$ passes through a maximum.

The amount of crosslinker b) in monomer solution 2 is preferably 0.01 to 0.50 mmol, more preferably 0.02 to 0.25 mmol and most preferably 0.05 to 0.15 mmol, based in each case on 1 mol of monomer a). Centrifuge retention capacity (CRC) and free swell rate (FSR) rise with falling crosslinker content.

Initiators c) used may be all compounds which generate free radicals under the polymerization conditions, for example thermal initiators, redox initiators or photoinitiators.

Suitable redox initiators are potassium peroxodisulfate or sodium peroxodisulfate/ascorbic acid, hydrogen peroxide/ascorbic acid, potassium peroxodisulfate or sodium peroxodisulfate/sodium bisulfite and hydrogen peroxide/sodium bisulfite. Preference is given to using mixtures of thermal initiators and redox initiators, such as potassium peroxodisulfate or sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Suitable thermal initiators are especially azo initiators, such as 2,2'-azobis[2-(2-imidazolin-2-yl)propane] dihydrochloride and 2,2'-azobis[2-(5-methyl-2-imidazolin-2-yl)propane] dihydrochloride, 2,2'-azobis(2-amidinopropane) dihydrochloride, 4,4''-azobis(4-cyanopentanoic acid), 4,4' and the sodium salts thereof, 2,2'-azobis[2-methyl-N-(2-hydroxyethyl)propionamide] and 2,2'-azobis(imino-1-pyrrolidino-2-ethylpropane) dihydrochloride.

Suitable photoinitiators are, for example, 2-hydroxy-2-methylpropiophenone and 1-[4-(2-hydroxyethoxy)phenyl]-2-hydroxy-2-methyl-1-propan-1-one.

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Optionally, one or more chelating agents may be added to the monomer solution or starting materials thereof to mask metal ions, for example iron, for the purpose of stabilization. Suitable chelating agents are, for example, alkali metal citrates, citric acid, alkali metal tartrates, pentasodium triphosphate, ethylenediamine tetraacetate, nitrilotriacetic acid, and also all chelating agents known by the Trilon® name, for example Trilon® C (pentasodium diethylenetriaminepentaacetate), Trilon® D (trisodium (hydroxyethyl) ethylenediaminetriacetate), and Trilon® M (methylglycinediacetic acid).

The polymerization of monomer solution 1 is not subject to any restrictions. It is possible to use any known polymerization processes, for example solution polymerization, inverse suspension polymerization and dropletizing polymerization.

Solution polymerization involves polymerizing monomer solution 1, for example in a kneading reactor or belt reactor. In the kneading reactor, the polymer gel formed in the polymerization of monomer solution 1 is comminuted continuously by, for example, contrarotatory stirrer shafts, as described in WO 2001/038402 A1. Polymerization in a belt reactor is described, for example, in DE 38 25 366 A1 and U.S. Pat. No. 6,241,928. Polymerization in a belt reactor forms a polymer gel which has to be comminuted in a further process step, for example in an extruder or kneader.

Subsequently, the polymer gel obtained by solution polymerization is dried, comminuted and classified. This removes excessively small polymer particles ("fines"). For this purpose, it is possible to use sieves having a mesh size of 250 µm or less, preferably 200 µm or less, more preferably 150 µm or less and most preferably 120 µm or less.

Inverse suspension polymerization involves suspending monomer solution 1 in a hydrophobic solvent. Subsequently, the resulting polymer particles are subjected to azeotropic dewatering, separated from the solvent by filtration and dried.

Inverse suspension polymerization can likewise remove excessively small polymer particles ("fines").

Dropletizing polymerization involves polymerizing droplets of monomer solution 1 in a surrounding gas phase. It is possible here to combine the process steps of polymerization and drying, as described in WO 2008/040715 A2, WO 2008/052971 A1 and WO 2011/026876 A1. Excessively small polymer particles ("fines") are entrained with the gas stream and have to be removed therefrom. For this purpose, it is possible to use filters or cyclones.

The polymer particles which have been obtained by polymerizing monomer solution 1 and removed and have a particle size of 250 µm or less, preferably 200 µm or less, more preferably 150 µm or less and most preferably 120 µm or less are agglomerated.

For agglomeration, the polymer particles are dispersed in a hydrophobic solvent.

Usable hydrophobic solvents are all the solvents known to the person skilled in the art for use in suspension polymerization. Preference is given to using aliphatic hydrocarbons, such as n-hexane, n-heptane, n-octane, n-nonane, n-decane, cyclohexane or mixtures thereof. Hydrophobic solvents have a solubility in water at 23° C. of less than 5 g/100 g, preferably less than 1 g/100 g, more preferably less than 0.5 g/100 g.

The hydrophobic solvent boils within the range from preferably 50 to 150° C., more preferably 60 to 120° C., most preferably 70 to 90° C.

The ratio between hydrophobic solvent and polymer particles is 0.2 to 3.0, preferably 0.3 to 2.7 and very preferably from 0.4 to 2.4.

For dispersion of the polymer particles in the hydrophobic solvent or for dispersion of the superabsorbent particles which form, it is possible to add dispersing aids. These dispersing aids may be anionic, cationic, nonionic or amphoteric surfactants, or natural, semisynthetic or synthetic polymers.

Anionic surfactants are, for example, sodium polyoxyethylene dodecyl ether sulfate and sodium dodecyl ether sulfate. A cationic surfactant is, for example, trimethylstearylammonium chloride. An amphoteric surfactant is, for example, carboxymethyldimethylcetylammonium. Nonionic surfactants are, for example, sucrose fatty acid esters, such as sucrose monostearate and sucrose dilaurate, sorbitan esters such as sorbitan monostearate, trehalose fatty acid esters, such as trehalose stearate, polyoxyalkylene compounds based on sorbitan esters, such as polyoxyethylenesorbitan monostearate.

Suitable polymers are, for example, cellulose derivatives such as hydroxyethyl cellulose, methyl hydroxyethyl cellulose, methyl hydroxypropyl cellulose, methyl cellulose and carboxymethyl cellulose, polyvinylpyrrolidone, copolymers of vinylpyrrolidone, gelatin, gum arabic, xanthan, casein, polyglycerols, polyglycerol fatty acid esters, polyethylene glycols, modified polyethylene glycol such as polyethylene glycol stearate or polyethylene glycol stearyl ether stearate, polyvinyl alcohol, partially hydrolyzed polyvinyl acetates and modified polyethylene, such as a maleic acid-modified polyethylene.

It is also possible to use inorganic particles as dispersing aids, these being called Pickering systems. Such a Pickering system may consist of the solid particles on their own or additionally of auxiliaries which improve the dispersibility of the particles in water or the wettability of the particles by the hydrophobic solvent. The way in which they work and their use are described in WO 99/24525 A1 and EP 1 321 182 A1.

The inorganic solid particles may be metal salts, such as salts, oxides and hydroxides of calcium, magnesium, iron, zinc, nickel, titanium, aluminum, silicon, barium and manganese. These include magnesium hydroxide, magnesium carbonate, magnesium oxide, calcium oxalate, calcium carbonate, barium carbonate, barium sulfate, titanium dioxide, aluminum oxide, aluminum hydroxide and zinc sulfide. These likewise include silicates, bentonite, hydroxyapatite and hydrotalcites. Particular preference is given to $SiO_2$-based silicas, magnesium pyrophosphate and tricalcium phosphate.

Suitable $SiO_2$-based dispersing aids are finely divided silicas. These can be dispersed in water as fine solid particles. It is also possible to use what are called colloidal dispersions of silica in water. Such colloidal dispersions are alkaline aqueous mixtures of silica. In the alkaline pH range, the particles are swollen and stable in water. Preferred colloidal dispersions of silica, at pH 9.3, have a specific surface area in the range from 20 to 90 $m^2/g$.

In addition, it is possible to use any desired mixtures of the dispersing aids.

The dispersing aid is typically dissolved or dispersed in the hydrophobic solvent. The dispersing aid is used in amounts between 0.01% and 10% by weight, preferably between 0.2% and 5% by weight and more preferably between 0.5% and 2% by weight, based on the monomer solution.

The performance of the agglomeration is known to those skilled in the art and is not subject to any restrictions.

A monomer solution 2 is metered into the dispersed polymer particles and polymerization is effected again. The polymer particles do not agglomerate until the second polymerization.

Monomer solution 1 and monomer solution 2 may be identical or different in terms of composition.

With every further addition of monomer to agglomerates that have already formed, the agglomerates can agglomerate further to form larger agglomerates.

There may be cooling steps between the metered additions of monomer. Some of the dispersing aid may precipitate out therein.

Advantageously, several stirred reactors are connected in series for the multistage agglomeration. Through postreaction in further stirred reactors, the monomer conversion can be increased and backmixing can be reduced.

The agglomeration is preferably conducted under reduced pressure, for example at a pressure of 800 mbar. The pressure can be used to set the boiling point of the reaction mixture to the desired reaction temperature.

In a preferred embodiment of the present invention, the superabsorbent particles are subjected to azeotropic dewatering in the polymer dispersion and filtered out of the polymer dispersion, and the filtered superabsorbent particles are dried to remove the adhering residual hydrophobic solvent.

To further improve the properties, the resulting superabsorbent particles may be thermally surface postcrosslinked. The thermal surface postcrosslinking can be conducted in the polymer dispersion or with the superabsorbent particles which have been removed from the polymer dispersion and dried.

Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are alkylene carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 2003/031482 A1.

In addition, it is also possible to use surface postcrosslinkers which comprise additional polymerizable ethylenically unsaturated groups, as described in DE 37 13 601 A1.

In addition, it is possible to use any desired mixtures of the suitable surface postcrosslinkers.

Preferred surface postcrosslinkers are alkylene carbonates, 2-oxazolidinones, bis- and poly-2-oxazolidinones, 2-oxotetrahydro-1,3-oxazines, N-acyl-2-oxazolidinones, cyclic ureas, bicyclic amido acetals, oxetanes, bisoxetanes and morpholine-2,3-diones.

Particularly preferred surface postcrosslinkers are ethylene carbonate (1,3-dioxolan-2-one), trimethylene carbonate (1,3-dioxan-2-one), 3-methyl-3-oxetanemethanol, 2-hydroxyethyl-2-oxazolidinone, 2-oxazolidinone and methyl-2-oxazolidinone.

Very particular preference is given to ethylene carbonate.

The amount of surface postcrosslinker is preferably 0.1% to 10% by weight, more preferably 0.5% to 7.5% by weight and most preferably 1% to 5% by weight, based in each case on the polymer particles.

The surface postcrosslinkers are typically used in the form of an aqueous solution. The amount of the solvent is preferably 0.001% to 8% by weight, more preferably 2% to 7% by weight, even more preferably 3% to 6% by weight and especially 4% to 5% by weight, based in each case on the polymer particles. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 10:90 to 60:40.

In a preferred embodiment of the present invention, cations, especially polyvalent cations, are applied to the particle surface in addition to the surface postcrosslinkers before, during or after the thermal surface postcrosslinking.

The polyvalent cations usable in the process of the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001% to 1.5% by weight, preferably 0.005% to 1% by weight and more preferably 0.02% to 0.8% by weight, based in each case on the polymer particles.

The surface postcrosslinking is typically performed in such a way that a solution of the surface postcrosslinker is sprayed onto the dried polymer particles. After the spray application, the surface postcrosslinker-coated polymer particles are thermally surface postcrosslinked.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The thermal surface postcrosslinking is preferably performed in contact driers, more preferably paddle driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and thermal surface postcrosslinking in a fluidized bed drier.

It may be advantageous to conduct the thermal surface postcrosslinking under reduced pressure or to conduct it with use of drying gases, for example dried air and nitrogen, in order to ensure the very substantial removal of the solvents.

Subsequently, the surface postcrosslinked polymer particles can be classified, with removal of excessively small and/or excessively large polymer particles and recycling thereof into the process.

The surface postcrosslinking can also be conducted in the polymer dispersion. For this purpose, the solution of the surface postcrosslinker is added to the polymer dispersion. In this context, it may be advantageous to conduct the thermal surface postcrosslinking under elevated pressure, for example with use of hydrophobic organic solvents having a boiling point at 1013 mbar below the desired temperature for the thermal surface postcrosslinking. After the thermal surface postcrosslinking in the polymer dispersion, the superabsorbent particles are dewatered azeotropically in the polymer dispersion and removed from the polymer dispersion, and the superabsorbent particles removed are dried to remove the adhering residual hydrophobic solvent.

Preferred surface postcrosslinking temperatures are in the range of 100 to 220° C., preferably in the range of 105 to 210° C., more preferably in the range of 110 to 205° C., most preferably in the range of 120 to 200° C. The preferred residence time at this temperature is preferably at least 10 minutes, more preferably at least 20 minutes, most preferably at least 30 minutes, and typically at most 120 minutes.

In a further preferred embodiment of the present invention, hydrophilizing agents are additionally applied before, during or after the thermal surface postcrosslinking, for example sugar alcohols such as sorbitol, mannitol and xylitol, water-soluble polymers or copolymers such as cellulose, polyethylene glycols, polyvinyl alcohols, polyvinylpyrrolidones and polyacrylamides.

In a preferred embodiment of the present invention, the superabsorbent particles are cooled after the thermal surface postcrosslinking in a contact drier. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the superabsorbent particles are cooled to 20 to 150° C., preferably 30 to 120° C., more preferably 40 to 100° C. and most preferably 50 to 80° C.

To further improve the properties, the polymer particles thermally surface postcrosslinked in a contact drier can be coated or remoisturized.

The remoisturizing is preferably performed at 30 to 80° C., more preferably at 35 to 70° C., most preferably at 40 to 60° C. At excessively low temperatures, the superabsorbent particles tend to form lumps, and, at higher temperatures, water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20 and Plantacare 818 UP and surfactant mixtures.

The superabsorbent particles are tested by means of the test methods described below.

Methods:

The measurements should, unless stated otherwise, be conducted at an ambient temperature of 23±2° C. and a relative air humidity of 50±10%. The water-absorbing polymers are mixed thoroughly before the measurement.

Moisture Content

The moisture content of the superabsorbent particles is determined by EDANA recommended test method No. WSP 230.3 (11) "Mass Loss Upon Heating".

Centrifuge Retention Capacity

The centrifuge retention capacity (CRC) is determined by EDANA recommended test method No. WSP 241.3(11) "Fluid Retention Capacity in Saline, After Centrifugation".

Free Swell Rate

To determine the free swell rate (FSR), 1.00 g (=W1) of the water-absorbing polymer particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker (=W2). The time interval required for the absorption, which has been measured with the stopwatch, is designated as t. The disappearance of the last liquid droplet on the surface is determined as the time t.

The free swell rate (FSR) is calculated therefrom as follows:

$$FSR[g/g\ s]=W2/(W1 \times t)$$

If the moisture content of the water-absorbing polymer particles, however, is more than 3% by weight, the weight W1 should be corrected to take account of this moisture content.

Particle Size Distribution

The median particle size and the breadth of the particle size distribution ($\sigma_\xi$) were determined analogously to EP 0 349 240 B1, using sieves having mesh sizes of 100 μm, 200 μm, 300 μm, 400 μm, 450 μm, 500 μm, 600 μm, 710 μm, 800 μm, 900 μm, 1000 μm, 1180 μm, 1400 μm, 1600 μm, 1700 μm, 2000 μm and 4000 μm.

The narrower the particle size distribution, the smaller the values for the particle size distribution $\sigma_\xi$.

Mean Sphericity (mSPHT)

The mean sphericity (mSPHT) is determined with the PartAn® 3001 L particle analyzer (Microtrac Europe GmbH; DE).

The sample to be analyzed is introduced into a funnel. The computer-controlled measurement system starts the metering device and ensures a continuous, concentration-regulated particle flow. The particles fall individually through the measurement shaft and generate high-contrast shadow images between light source and high-resolution camera. The light source is actuated by the camera and, because of very short exposure times, produces faultless image information for the multiple evaluation of each individual particle in real time.

In a 3D process, each particle is analyzed repeatedly and the process thus gives the absolute results for length, width, thickness, area and circumference. The number of pixels covered by the particle is used to calculate the size and shape. This also results in the comparatively precise determination of the mean sphericity (mSPHT).

EXAMPLE 1

A 2 L flange vessel equipped with impeller stirrer and reflux condenser was initially charged with 896.00 g of cyclohexane and 6.00 g of ethyl cellulose, and this initial charge was heated to 75° C. while stirring under nitrogen.

A monomer solution 1 prepared from 150.00 g (2.082 mol) of acrylic acid, 129.00 g (1.613 mol) of 50% by weight aqueous sodium hydroxide solution, 136.80 g of water, 0.0375 g (0.243 mmol) of N,N'-methylenebisacrylamide (MBA) and 0.50 g (1.850 mmol) of potassium peroxodisulfate was subsequently introduced into a feed vessel and purged with air. Monomer solution 1 was added dropwise at a stirrer speed of 450 rpm within 60 minutes. Monomer solution 1 was inertized with nitrogen immediately prior to the dropwise addition.

After feeding had ended, the mixture was stirred at 75° C. for a further 60 minutes. Subsequently, the reflux condenser was exchanged for a water separator and water was separated out.

The suspension present was cooled to 60° C. and the resultant polymer particles were filtered off with suction using a Büchner funnel with a paper filter. The further drying was effected at 45° C. in an air circulation drying cabinet and optionally in a vacuum drying cabinet at 800 mbar down to a residual moisture content of less than 15% by weight.

The resultant polymer particles had a centrifuge retention capacity (CRC) of 40.9 g/g, a free swell rate (FSR) of 0.09 g/gs, and a moisture content of 2.9% by weight.

EXAMPLE 2

A 2 L flange vessel equipped with impeller stirrer and reflux condenser was initially charged with 500.00 g of cyclohexane, 1.88 g of Span® 20 (sorbitan monostearate) and 60.00 g of superabsorbent particles from example 1, and this initial charge was heated to 70° C. while stirring under nitrogen.

A monomer solution 2 prepared from 50.00 g (0.694 mol) of acrylic acid, 43.00 g (0.538 mol) of 50% by weight aqueous sodium hydroxide solution, 45.60 g of water, 0.0125 g (0.081 mmol) of N,N'-methylenebisacrylamide (MBA) and 0.167 g (0.618 mmol) of potassium peroxodisulfate was introduced into a feed vessel and purged with air. Monomer solution 2 was added dropwise at a stirrer speed of 400 rpm within 30 minutes. Monomer solution 2 was inertized with nitrogen immediately prior to the dropwise addition.

After feeding had ended, the mixture was stirred at 70° C. for a further 60 minutes. Subsequently, the reflux condenser was exchanged for a water separator and water was separated out.

The suspension present was cooled to 60° C. and the resultant polymer particles were filtered off with suction using a Büchner funnel with a paper filter. The further drying was effected at 45° C. in an air circulation drying cabinet and optionally in a vacuum drying cabinet at 800 mbar down to a residual moisture content of less than 15% by weight.

The properties of the resultant polymer particles are summarized in table 1.

EXAMPLE 3

A 2 L flange vessel equipped with impeller stirrer and reflux condenser was initially charged with 500.00 g of n-heptane, 0.92 g of sucrose stearate (Ryoto® Sugar Ester S-370, Mitsubishi Chemical Europe GmbH, Düsseldorf, Germany) and 60.00 g of superabsorbent particles, and this initial charge was heated to an internal temperature of 70° C. while stirring under nitrogen, until the sucrose stearate had dissolved fully.

The superabsorbent particles were produced according to example 1 of WO 2014/079694 A1 and separated out of stream (8) in FIG. 1.

A monomer solution 2 prepared from 50.00 g (0.0694 mol) of acrylic acid, 43.00 g (0.538 mol) of 50% by weight aqueous sodium hydroxide solution, 45.60 g of water, 0.0125 g (0.081 mmol) of N,N'-methylenebisacrylamide (MBA) and 0.167 g (0.618 mmol) of potassium peroxosulfate was subsequently introduced into a feed vessel and purged with air. Monomer solution 2 was added dropwise at a stirrer speed of 400 rpm within 30 minutes. Monomer solution 2 was inertized with nitrogen immediately prior to the dropwise addition.

After feeding had ended, the mixture was stirred at 70° C. for a further 60 minutes. Subsequently, the reflux condenser was exchanged for a water separator and water was separated out.

The suspension present was cooled to 60° C. and the resultant polymer particles were filtered off with suction using a Büchner funnel with a paper filter. The further drying was effected at 45° C. in an air circulation drying cabinet and optionally in a vacuum drying cabinet at 800 mbar down to a residual moisture content of less than 15% by weight.

The properties of the resultant polymer particles are summarized in table 1.

EXAMPLE 4

The procedure was as in example 3, except that a monomer solution 2 prepared from 50.00 g (0.694 mol) of acrylic acid, 43.00 g (0.538 mol) of 50% by weight aqueous sodium hydroxide solution, 75.60 g of water, 0.0125 g (0.081 mmol) of N,N'-methylenebisacrylamide (MBA) and 0.167 g (0.618 mmol) of potassium peroxodisulfate was used.

The properties of the resultant polymer particles are summarized in table 1.

EXAMPLE 5

The procedure was as in example 3, except that a monomer solution 2 prepared from 50.00 g (0.694 mol) of acrylic acid, 43.00 g (0.538 mol) of 50% by weight aqueous sodium hydroxide solution, 93.60 g of water, 0.0125 g (0.081 mmol) of N,N'-methylenebisacrylamide (MBA) and 0.167 g (0.618 mmol) of potassium peroxodisulfate was used.

The properties of the resultant polymer particles are summarized in table 1.

TABLE 1

Properties of the agglomerated superabsorbents

| Example | Superabsorbent | Water % by wt. bop | CRC g/g | FSR g/gs | Moisture content % by wt. |
|---|---|---|---|---|---|
| 2 | suspension polymerization | 128 | 16.9 | 1.25 | 5.3 |
| 3 | dropletizing polymerization | 128 | 24.2 | 0.78 | 3.3 |
| 4 | dropletizing polymerization | 178 | 29.6 | 0.41 | 3.6 |
| 5 | dropletizing polymerization | 208 | 36.6 | 0.23 | 5.0 | bop based on superabsorbent particles (polymer)

The invention claimed is:

1. A process for agglomerating superabsorbent particles comprising (A) polymerizing a first aqueous monomer solution comprising
   a) at least one ethylenically unsaturated monomer which bears an acid group and optionally at least partly neutralized,
   b) optionally one or more crosslinker,
   c) at least one initiator,
   d) optionally one or more ethylenically unsaturated monomer copolymerizable with the monomer mentioned under a), and
   e) optionally one or more water-soluble polymer to provide polymer particles,
   optionally drying and/or comminuting the polymer particles, removing polymer particles having a particle size of 250 µm or less,
   dispersing the polymer particles having a particle size of 250 µm or less in a hydrophobic organic solvent,
   mixing the dispersed polymer particles with a second aqueous monomer solution comprising
   a) at least one ethylenically unsaturated monomer which bears an acid group and optionally at least partly neutralized,
   b) optionally one or more crosslinker,
   c) at least one initiator,
   d) optionally one or more ethylenically unsaturated monomer copolymerizable with the monomer mentioned under a), and
   e) optionally one or more water-soluble polymer,
   wherein the first aqueous monomer solution and the second aqueous monomer solution may be the same or different and a total amount of water applied to the dispersed polymer particles with the second aqueous monomer solution being at least 100% by weight, based on the dispersed polymer particles, and
   polymerizing the second aqueous monomer solution to provide agglomerated particle superabsorbent.

2. The process according to claim 1, wherein polymer particles having a particle size of 200 µm or less are removed and dispersed in the hydrophobic organic solvent.

3. The process according to claim 1, wherein polymer particles having a particle size of 150 µm or less are removed and dispersed in the hydrophobic organic solvent.

4. The process according to claim 1, wherein the amount of water applied with the second monomer solution is at least 150% by weight, based on the dispersed polymer particles.

5. The process according to claim 1, wherein the amount of water applied with the second monomer solution is at least 175% by weight, based on the dispersed polymer particles.

6. The process according to claim 1, wherein the second monomer solution comprises from 0.01 to 0.50 mmol of crosslinker b), based on 1 mol of monomer a).

7. The process according to claim 1, wherein the second monomer solution comprises from 0.02 to 0.25 mmol of crosslinker b), based on 1 mol of monomer a).

8. The process according to claim 1, wherein the second monomer solution comprises from 0.05 to 0.15 mmol of crosslinker b), based on 1 mol of monomer a).

9. The process according to claim 1, wherein the first monomer solution is polymerized by dropletizing polymerization.

10. The process according to claim 9, wherein the polymer particles are removed from an offgas of the dropletizing polymerization by means of a filter or cyclone.

11. The process according to claim 1, wherein the first monomer solution is polymerized by suspension polymerization and the resulting polymer particles are dried.

12. The process according to claim 1, wherein the first monomer solution is polymerized by solution polymerization and the resulting polymer particles are dried and comminuted.

13. The process according to claim 11, wherein the polymer particles are removed by means of a sieve having a mesh size of 250 µm or less.

14. The process according to claim 11, wherein the polymer particles are removed by means of a sieve having a mesh size of 200 µm or less.

15. The process according to claim 11, wherein the polymer particles are removed by means of a sieve having a mesh size of 150 µm or less.

16. The process according to claim 12, wherein the polymer particles are removed by means of a sieve having a mesh size of 250 µm or less.

17. The process according to claim 12, wherein the polymer particles are removed by means of a sieve having a mesh size of 200 µm or less.

18. The process according to claim 12, wherein the polymer particles are removed by means of a sieve having a mesh size of 150 µm or less.

19. A process for agglomerating superabsorbent particles comprising:
   (a) providing superabsorbent particles having a particle size of 250 µm or less;
   (b) dispersing superabsorbent particles in a hydrophobic organic solvent;
   (c) mixing the dispersed superabsorbent particles with an aqueous monomer solution comprising:
      i) at least one ethylenically unsaturated monomer which bears an acid group and optionally at least partly neutralized,
      ii) optionally one or more crosslinker,
      iii) at least one initiator,
      iv) optionally one or more ethylenically unsaturated monomer copolymerizable with the monomer mentioned under i), and
      v) optionally one or more water-soluble polymer,
   wherein a total amount of water applied to the dispersed superabsorbent particles with the aqueous monomer solution being at least 100% by weight, based on the dispersed polymer superabsorbent particles, and
   polymerizing the second monomer solution to provide agglomerated superabsorbent particles.

20. The process of claim 19 comprising providing superabsorbent particles having a particle size of 200 µm or less.

* * * * *